(12) United States Patent
Lodder

(10) Patent No.: US 7,557,923 B2
(45) Date of Patent: Jul. 7, 2009

(54) METHOD AND SYSTEM FOR IN SITU SPECTROSCOPIC EVALUATION OF AN OBJECT

(75) Inventor: Robert A. Lodder, Nicholasville, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 398 days.

(21) Appl. No.: 11/519,269

(22) Filed: Sep. 12, 2006

(65) Prior Publication Data

US 2007/0058170 A1    Mar. 15, 2007

Related U.S. Application Data

(60) Provisional application No. 60/716,071, filed on Sep. 12, 2005.

(51) Int. Cl.
*G01J 3/50* (2006.01)
(52) U.S. Cl. ............. 356/407; 356/402; 356/425; 250/226
(58) Field of Classification Search .......... 356/407, 356/402, 425, 447, 448; 250/226
See application file for complete search history.

(56) References Cited

U.S. PATENT DOCUMENTS

| | | | |
|---|---|---|---|
| 5,498,875 A | 3/1996 | Obremski et al. | |
| 5,774,213 A | 6/1998 | Trebino et al. | |
| 5,844,680 A | 12/1998 | Sperling | |
| 6,124,936 A | 9/2000 | Okamoto | |
| 6,542,245 B2 | 4/2003 | Toida | |
| 6,674,530 B2 | 1/2004 | Berstis | |
| 6,690,464 B1 | 2/2004 | Lewis et al. | |
| 6,721,692 B2 | 4/2004 | Mestha et al. | |
| 6,795,195 B1 | 9/2004 | Barbour et al. | |
| 6,825,929 B2 | 11/2004 | Dorsel | |
| 6,888,633 B2 | 5/2005 | Vander Jagt et al. | |
| 6,952,263 B2 | 10/2005 | Weiss et al. | |
| 7,170,599 B2 * | 1/2007 | Cunningham et al. | 356/326 |
| 7,251,031 B2 * | 7/2007 | Lewis et al. | 356/407 |
| 2003/0227626 A1 | 12/2003 | Dobbs et al. | |
| 2005/0168738 A1 | 8/2005 | Ohnishi et al. | |
| 2005/0280817 A1 | 12/2005 | Horchner et al. | |

\* cited by examiner

*Primary Examiner*—L. G Lauchman
(74) *Attorney, Agent, or Firm*—King & Schickli, PLLC

(57) ABSTRACT

A method and system for spectroscopically determining surface and product characteristics is employed for rapid detection of product characteristics and/or the presence or absence of suspected analytes, and the concentration of the analyte. The method and system uses a signal wide band detector that does not require focusing optics in many environments. It can be used for cleaning validation of pharmaceutical products and process equipment.

23 Claims, 7 Drawing Sheets

METHOD AND SYSTEM FOR IN SITU SPECTROSCOPIC EVALUATION OF AN OBJECT

This application claims the benefit of the U.S. Provisional Patent Application Ser. No. 60/716,071, filed Sep. 12, 2005.

This invention was made with Government support under the NSF IGERT program. The Government may have certain rights in this invention.

TECHNICAL FIELD

The present invention relates generally to the spectroscopic evaluation of analytes and objects, and more specifically to a spectroscopic method and system for quickly determining the presence or absence of an analyte of interest or the presence or absence of desired characteristics of an object.

BACKGROUND OF THE INVENTION

In recent years, the issue of cleaning validation in pharmaceutical manufacturing processes has grown significantly. The purpose of cleaning validation is to accurately verify that potentially harmful compounds have been removed (below acceptable limits) from surfaces in process equipment prior to its use for another purpose. In the pharmaceutical industry, the need for adequate verifiable cleaning, and thus cleaning validation, occurs in a number of instances, as for example when equipment is used for processing two or more different active pharmaceutical ingredients sequentially or wherever cross-contamination between the products can have deleterious consequences. Additionally, it may be desirable to insure that the surfaces of process equipment do not contain residue from cleaning agents used in the cleaning process. Adequate cleaning of pharmaceutical process equipment is essential for the production of high quality pharmaceuticals, the elimination of contaminated drugs, and the avoidance of disruption of the manufacturing processes (with the possible consequence of losing the availability of essential drugs).

Increased interest in cleaning validation during the past several years has been driven by a number of factors. One factor for this increased interest is the attentiveness to cleaning validation by regulatory agencies. Highly publicized instances of pharmaceutical contamination, such as the 2004 contamination of approximately one-half of the United States influenza vaccine, are likely to further enhance industry awareness and regulatory attentiveness to the problem. Another factor for the increased interest is the trend toward the use of pharmaceutical manufacturing equipment and facilities for the manufacture of multiple products to increase manufacturing efficiency. A rapid, inexpensive verifiable method of validating adequate cleaning of pharmaceutical process equipment and process line significantly promotes the economic viability of using the equipment for multiple products. Among other advantages, utilizing pharmaceutical manufacturing equipment and facilities for multiple products facilitates cost-efficient development of pharmaceuticals for smaller demographics.

Prior art approaches to cleaning validation have focused upon collecting samples of residues on the surfaces to be validated, followed by quantitative analysis of the collected samples. Traditionally, this has been done either by analyzing samples collected by swabbing a portion of the surface or by analyzing a rinse matrix collected after the surface has been cleaned. These prior art methods have substantial shortcomings. Swabbing techniques require manually swabbing the entire surface of interest to assure complete coverage, and necessitate time-consuming analysis of the swabs. Additionally, manual swabbing procedures are prone to incomplete analyte recovery from the surface or the swap. Total analysis time for the swabbing technique is extensive, resulting in lengthy downtimes for the pharmaceutical process equipment. Although rinse matrix testing does include sampling from the entire surface, this technique includes a more difficult method validation, dilution and analyte solubility and detachment issues. Like the swabbing technique, rinse testing disadvantageously requires estimation of the quantity of analyte remaining on the surface.

It also is desirable to evaluate pharmaceutical products for certain desired characteristics. For example, in the manufacture of pharmaceutical tablets, it is desirable to control such characteristics as the hardness and moisture content of drugs in tablet form. Appropriate hardness of the tablet insures that the tablet will meet any required friability standards by retaining its structural integrity and not crumbling or powderizing prior to usage. Control of the moisture content of pharmaceutical tablets also is important, particularly for biotechnology products. Moisture content below an optimal level may allow the ingredients of the tablet to denature. Moisture content above an optimal level may allow the ingredients of the tablet to react. While tablets and other object can be tested for characteristics such as hardness and moisture content, prior art testing for these characteristics typically is conducted only on a sample basis (as for example on a sample size equal to the square root of n+1 for n tablets), involves substantial time and effort, and results in destruction of the tested samples.

SUMMARY OF THE INVENTION

It is an object of at least one embodiment of the present invention to obviate one or more of the shortcomings of prior art cleaning validation methods.

It is another object of at least one embodiment of the present invention to provide an improved method and system for in situ rapidly determining the presence or absence of an analyte of interest.

Another object of at least one embodiment is to provide a method and system for rapidly determining the concentration of an analyte of interest in situ.

It is an object of another embodiment to provide a method and system for mapping the locations of different anyaltes.

A further object of at least one embodiment is to provide a method and system for simultaneously mapping the locations and concentrations of different analytes.

An object of at least one embodiment of the present invention is to provide a method and apparatus that eliminates the inadequacies associated with surface sampling procedures for cleaning validation procedures in pharmaceutical process equipment.

It is an object of at least one embodiment of the present invention to provide a rapid method for determining the presence or absence of contaminants on surfaces of pharmaceutical process equipment.

Another object of at least one embodiment is to provide a remote spectroscopic cleaning validation system for pharmaceutical process equipment that does not require imaging optics.

A further object of another embodiment of the invention is to provide a system and method for quickly spectroscopically evaluating a pharmaceutical or non-pharmaceutical object for characteristics of interest.

The above objects are provided merely as non-limiting examples, and do not define the present invention or necessarily apply to every aspect thereof. Additional objects, advantages and other novel features of the invention will be set forth in part in the description that follows and will also become apparent to those skilled in the art upon consideration of the teachings of the invention.

To achieve one or more of these objects, one embodiment of the present invention includes a system for determining in situ the presence of an analyte film, such as a biofilm or other chemical film or residue, on the surface of an object. The system includes a collimated light emitting array source capable of emitting modulated light pulses having a plurality of different wavelengths of light aimed at a plurality of different locations on a target surface of an article to be tested. The light emitting source modulates each of the different wavelengths with a modulation uncorrelated to each of the other different wavelengths so as to substantially eliminate covariance between light of differing wavelengths. The amount of light energy per unit time that is emitted toward the target surface also may be varied. A wide band light detector for receiving light scattered back from the target surface is provided without intervening focusing optics. A processor for calculating the covariance between scattered light received by the light detector and the pulse sequence applied to each collimated light emitting array element is provided for calculating and generating a signal representative of the presence or absence of an analyte or characteristic of interest. The light detected over a multiple of wavelengths can be used to generate a signal representative of the analyte concentration.

In one exemplary embodiment, the amount of light energy per unit time emitted toward the target surface is varied by varying the intensity of light emitted at different modulations of the plurality of the wavelengths.

In another exemplary embodiment, the amount of light energy per unit time emitted toward the target surface is varied by varying the duty cycle of the emitted light.

According to one exemplary embodiment, the light emitting source modulates each of the pulses of different wavelengths with a different orthogonal pulse sequence uncorrelated to the other modulated wavelengths, and the amount of light per unit time emitted toward the target surface is varied by varying the duty cycle of the pulses.

In another exemplary embodiment, a memory is associated with the processor, and the memory has at least one stored table of spectral emission values representative of discriminating spectral reflectance characteristics of an analyte of interest. The signals observed at the detector are dependent upon the correspondence between the scattered light received by the detector and the spectral emission values in at least one of the stored tables.

According to another exemplary embodiment, the memory has a plurality of stored tables of spectral reflectance values, the plurality of stored tables having spectral reflectance values representative of multiple levels of concentration of an analyte of interest.

In another embodiment, a method for analyzing a surface of interest is provided. At least one table of spectral reflectance values representative of discriminating spectral reflectance characteristics of an analyte of interest is created. Modulated light having a plurality of different wavelengths of collimated light with different modulations of the plurality of wavelengths is directed toward the surface. The different modulations are uncorrelated to each of the other modulated wavelengths so as to substantially eliminate covariance between light of differing wavelengths. A single wide band detector is used for detecting light scattered back from the surface in at least the ultraviolet, visible light and infrared ranges of the electromagnetic spectrum. A signal is generated when the scattered light detected by the detector corresponds to the spectral emission values in at least one of the tables.

According to another exemplary embodiment, the plurality of wavelengths of collimated light emitted toward the surface are selected to correspond to discriminating scattering and absorption bands of an analyte of interest.

In another exemplary embodiment, the light detector receives scattered light from the surface without intervening focusing optics.

In another exemplary embodiment, the amount of light energy per unit time emitted toward the surface is varied selectively among the different modulations of wavelengths to vary the amount of scattered light from an analyte of interest as a function of the analyte's concentration.

In another exemplary embodiment, the selection of wavelengths emitted from the light source and the spectral reflectance values in at least one table are empirically derived.

According to another exemplary embodiment, a system for validating cleaning of pharmaceutical process equipment is provided. The system includes a light emitting array source capable of emitting modulated light pulses having a plurality of different wavelengths of collimated light toward a target surface of pharmaceutical process equipment to be tested. The light emitting source modulates the pulses of each of the different wavelengths with a different orthogonal pulse sequence relative to the other modulated wavelengths so as to substantially eliminate covariance between pulses of differing wavelength. A wide band light detector is provided for detecting light scattered from the target surface in at least the ultraviolet, visible light and infrared ranges of the electromagnetic spectrum, the detector being spaced from the light emitting source. A processor has a memory associated with it having at least one stored table of spectral emission values representative of discriminating spectral reflectance characteristics of an analyte of interest. The processor is operative to generate a signal in response to correspondency between scattered light received by the detector and the spectral emission values in at least one table.

In another embodiment, the light emitting source includes an array of light-emitting laser diodes arranged in a predetermined spatial relationship to the other diodes with the position of each diodes selected to correspond to a different position of the target surface.

In another exemplary embodiment, a method is provided for determining whether a pharmaceutical product has a predetermined attribute. At least one table of spectral emission values representative of at least one discriminating spectral reflectance characteristic of a predetermined attribute of a pharmaceutical product is created. Modulated light is emitted having a plurality of different wavelengths of collimated light directed toward the product with the different modulations of the plurality of wavelengths being uncorrelated to each of the other modulated wavelengths so as to substantially eliminate covariance between light of differing wavelengths. A single detector is used for detecting light scattered back from the product and a signal is generated when the scattered light received by the detector corresponds to the spectral emission values in at least one of the tables.

In another exemplary embodiment, a method is provided for determining whether a pharmaceutical product has a predetermined physical feature or location. At least one table of spatial emission values representative of at least one discriminating spatial characteristic of a predetermined attribute of a pharmaceutical product is created. Modulated light is emitted having a plurality of different wavelengths of collimated light directed toward the product with the different wavelengths of light being uncorrelated to each of the other modulated wavelengths so as to substantially eliminate covariance between light of differing wavelengths. Modulated light is also emitted having a plurality of different aim points of collimated light toward the product with the different modulations of the plurality of aim points being uncorrelated to each of the other modulated aim points so as to substantially eliminate covariance between light of differing aim points. A single detector is used for detecting light scattered back from the product and a signal is generated when the scattered light received by the detector corresponds to the spatial emission values in at least one of the tables.

BRIEF DESCRIPTION OF THE DRAWINGS

The accompanying drawings incorporated in and forming a part of the specification, illustrate several aspects of the invention, and together with the description serves to explain the principles of the invention. In the drawings.

Reference will now be made in detail to exemplary embodiments of the invention, an example of which is illustrated in the accompanying drawings.

DETAILED DESCRIPTION OF EXEMPLARY EMBODIMENTS

The exemplary illustrated embodiments relate to a system for validating cleaning procedures on surfaces, particularly for surfaces of pharmaceutical process equipment. These exemplary embodiments spectroscopically examine target surfaces in situ to determine the presence or absence of particular analytes on the surfaces, and, if the analyte is present, to determine whether the amount of the analyte is below acceptable limits. In general, a target surface of interest is illuminated simultaneously with sequenced light pulses of different wavelengths at different locations from a light emitting array source. The wavelengths of light directed toward the target surface are selected to correspond to absorbances or other characteristics of the analyte of interest. Light returned from the target surface is collected and the light scatter in the returned light is measured and used to determine whether the analyte of interest is present, and if so, the concentration of the analyte.

Figure 1:
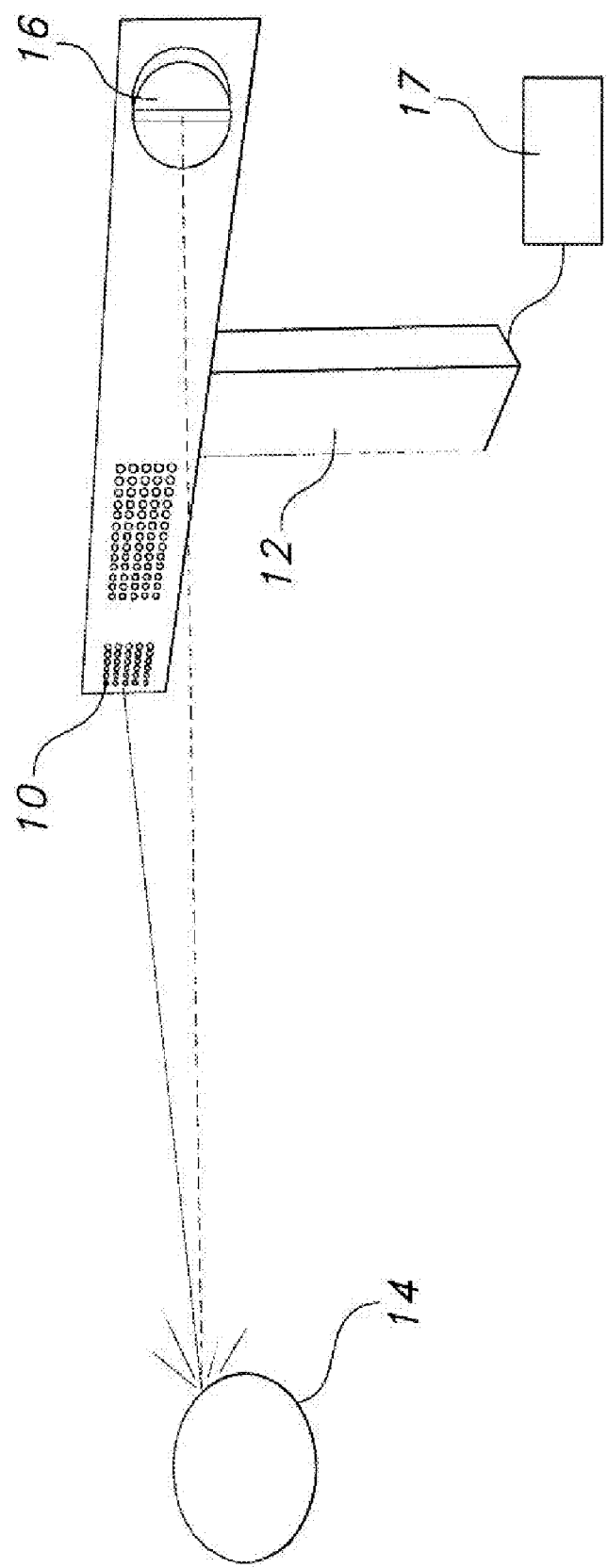
FIG. 1 is a schematic representation of system for remote in situ cleaning validation of target surface.

As schematically illustrated in the drawing of FIG. 1, the system includes a light emitting source, generally designated by the numeral 10. The light emitting array source 10 is mounted on a mast 12, and is directed to emit collimated light on a target surface 14. The emitted light has a plurality of wavelengths, with the different modulations of each emitter (wavelengths and aiming points) being uncorrelated to each of the other wavelengths and aiming points so as to substantially eliminate covariance between light of different emitting elements. As will be explained in greater detail below, the amount of light per unit time may be varied among the different wavelengths to facilitate quantification of the concentration of an analyte of interest.

The target surface 14 can be any surface to be tested for the presence or absence of an analyte of interest, as for example a land or soil surface. For purposes of describing the particular exemplary embodiment illustrated in the drawings, however, the target surface 14 will be assumed to represent a surface of pharmaceutical processing equipment. The mast 12 also supports a light detector 16, which is spaced from the emitting source by as much distance as practical to permit the light detector 16 to detect diffusely scattered light instead of specular reflectance. In the exemplary embodiment illustrated, the light detector is single multicolor detector capable of detecting scattered light in at least the ultraviolet, visible light and infrared ranges of the electromagnetic spectrum. A processor 17 (including a memory) receives a signal from the light detector 16 and calculates the covariance of the scattered light it receives. The processor 17 then compares the scattered light values received to spectral reflectance values stored in at least one table in the processor's memory.

Figure 2:
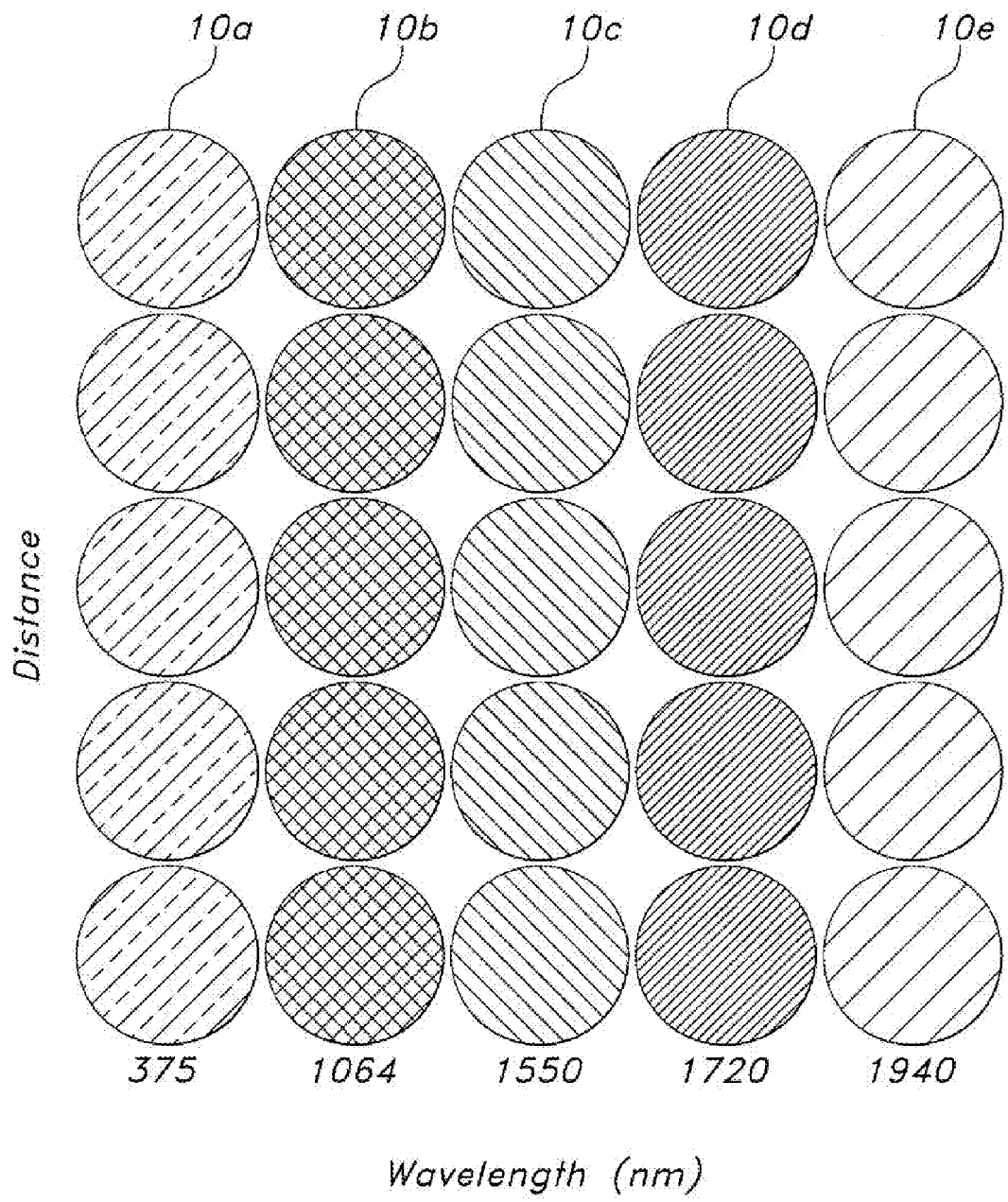
FIG. 2 is schematic representation of an array of laser diodes for sequentially emitting light pulses toward a target surface.

One potential type of light emitting source 10 is depicted in FIG. 2. This particular exemplary embodiment includes a rectangular array of laser diodes. Although the specifically illustrated embodiment utilizes a rectangular array, many other types of light emitting sources can be used. In the form illustrated, the array is formed of columns and rows, with each column of the array emitting a light at a certain wavelength. In one exemplary embodiment, the light emitting source emits radiation with multiple wavelengths in the near-infrared range, i.e, from 770 nm to approximately 3100 nm. The wavelengths selected for a particular application, however, are dependent upon the analyte on the target surface to be tested. More specifically the wavelengths are selected to correspond to the characteristic absorbencies of the analyte of interest. As specifically illustrated, the array includes five columns of diodes, designed by the designations 10a, 10b, 10c, 10d, and 10e. The diodes of the columns 10a through 10e respectively emit light at wavelengths of 375 nm, 1064 nm, 1550 nm, 1720 nm and 1940 nm. These particular wavelengths were selected for purposes of illustration in the illustrated exemplary embodiment to detect the presence or absence of bovine serum albumin on the target surface 14. The illustrated diodes 10 also have a predetermined spatial relationship. In the spatial relationship shown in FIG. 2, the vertical positions of the diodes of the array correspond to different vertical positions on the target surface 14. Each of the wavelengths of light are aimed at a plurality of different locations on the target surface of the article to be tested. The set of wavelengths is independent of the set of aiming locations. Thus, as illustrated, a rectangular array of emitters, each with a unique pulse sequence, is used to interrogate an article to be tested.

In accordance with the principles of one exemplary embodiment of the invention, the laser diodes of light emitting source 10 are specially modulated to permit the construction of a rugged, inexpensive cleaning validation system. When used for relative short distances, one of the embodiments of the system advantageously does not require a light detector with fragile lenses or focusing optics. In this regard, it is noted that the light detector 16 advantageously receives scattered light from the target surface 14 without intervening focusing optics. The ability to receive and analyze scattered light without focusing optics not only reduces cost, it permits use of the system in rugged environments where there would be a high risk of damage to fragile lenses. Nevertheless, if necessary for long distances or if desired, the system could be used with accessories, such as a compound parabolic concentrator, to enhance the detectability of the scattered light.

Each individual diode of the light emitting source 10 is modulated to emit a pulse of light with a different orthogonal pulse sequence that substantially eliminates covariance with pulses from the remaining diodes. This mutually exclusive sequencing of light pulses from the diodes is illustrated by the waveforms in FIG. 3 for three diodes. As is apparent from this graphical representation of the pulse sequences, there is a unique combination of pulses for any time interval. Such sequencing makes it possible to measure both total scattered light and to differentiate between the light scattered from the various modulations. With such sequencing, it is possible to detect and distinguish between scattered light from each of the diodes with a single wide band light detector 16. More specifically, each of the different wavelengths of collimated light is modulated so that it is uncorrelated to the modulation of any other wavelength, and covariance between light at differing wavelengths is substantially eliminated. While the illustrated embodiment is modulated with orthogonal pulse sequences, other forms of modulation may be used.

Figure 3:
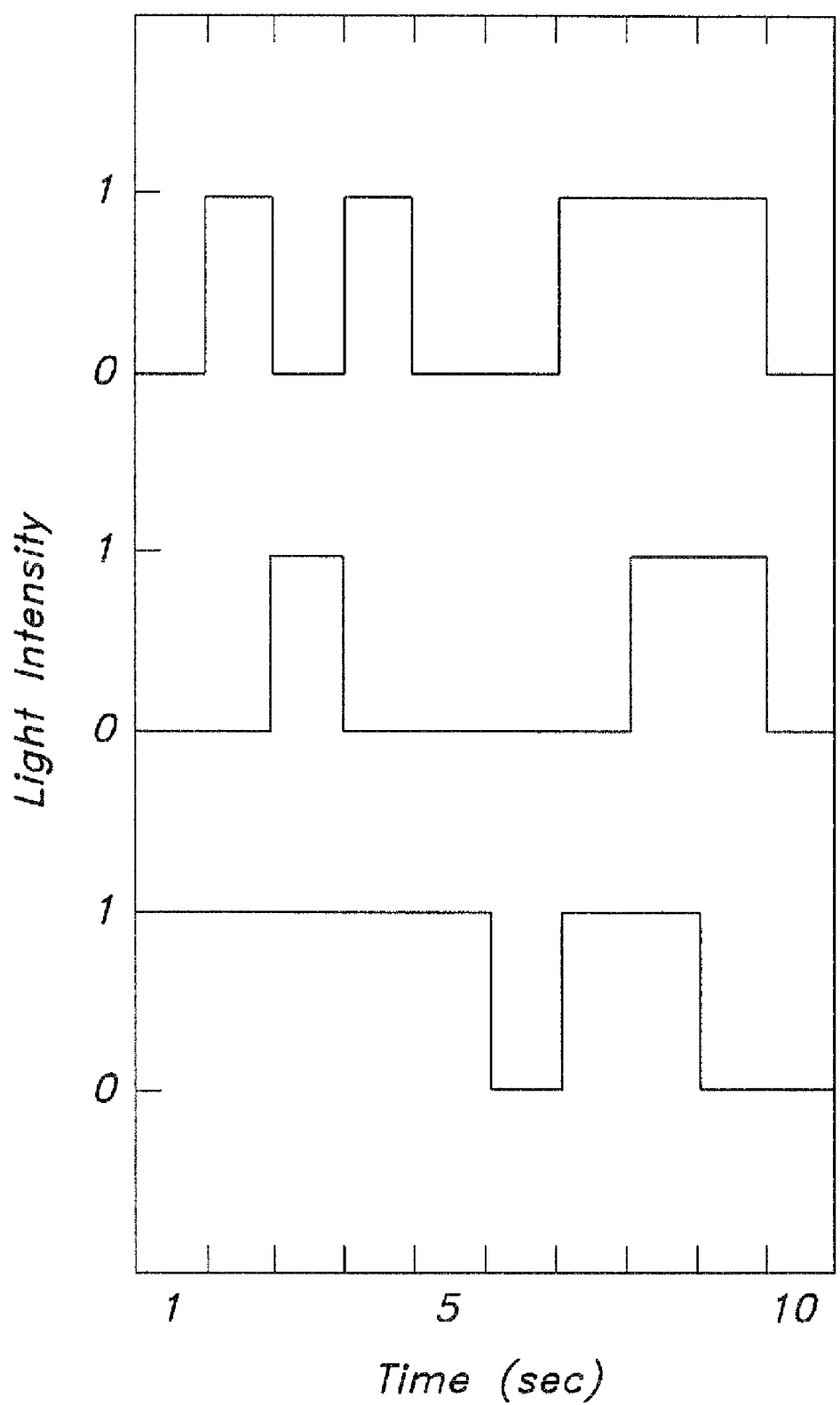
FIG. 3 is graph depicting representative orthogonal pulse sequencing for three laser diodes.
Figure 4:
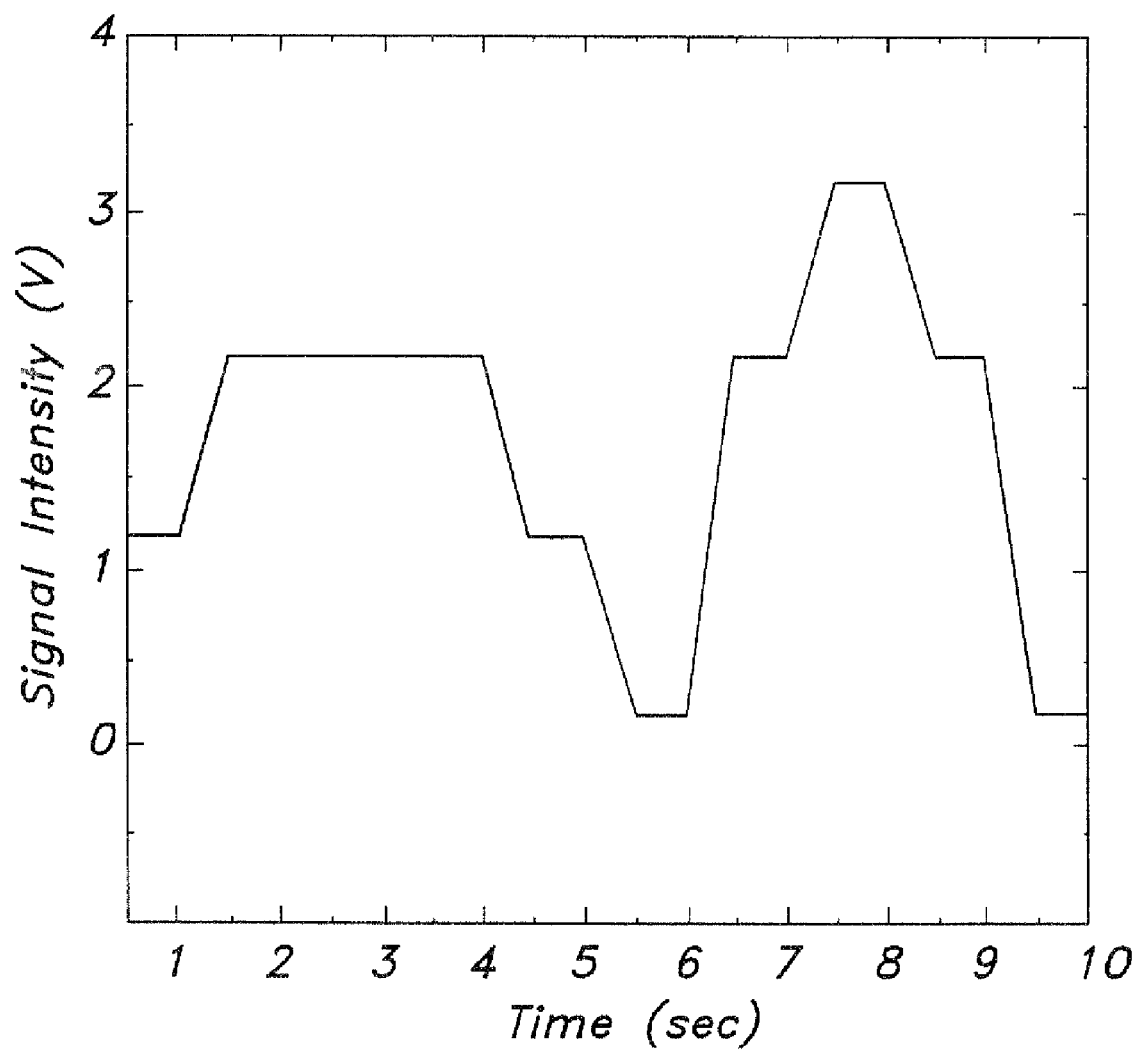
FIG. 4 is graph depicting the sum waveform of three scattered light signals returned from a target surface and received by a photodetector.

FIG. 4 shows an exemplary complex waveform collected by the light detector 16. The light collected by detector 16 includes light scattered from the interaction of the emitted light and the analyte on the surface of the target surface 14. Thus, unlike the zero covariance of the wavelengths emitted from the light emitting source 10, there is covariance in the light detected by detector 16. For this reason, a comparison between the waveforms of FIGS. 3 and 4 shows that the waveform of FIG. 4 differs from a waveform that would result from merely summing the individual waveforms shown in FIG. 3. Since the covariance between the light emitted from the individual diodes comprising the light source 10 is substantially zero, the covariance between the pulse sequence applied to each diode and the light detected by the detector 16 is representative of the intensity of scattered light from the target surface at the position and wavelength specified by the diode with that modulation sequence.

Figure 5:
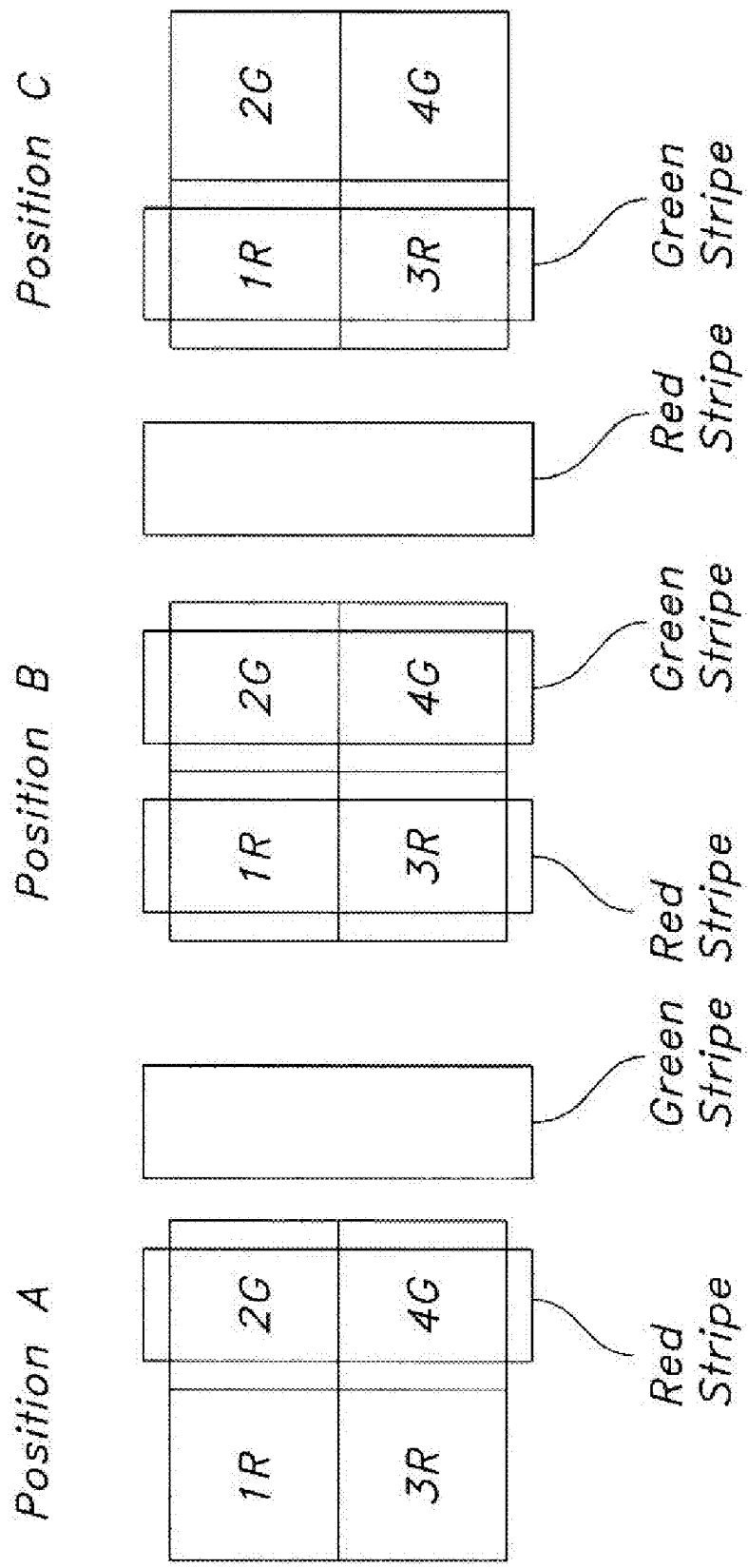
FIG. 5 is a schematic depiction illustrating how a simplified light emitting array can be used to identify the existence and location of an attribute on a target surface from spectral emission characteristics.

A simple example will illustrate how the location and existence of a predetermined characteristic can be identified on a target surface. In FIG. 5, a LED array consisting of two red LEDs, 1R and 3R and two green LEDs, 2G and 4G is schematically shown illuminating 3 different locations on a target surface containing a vertical red stripe and a vertical green strip. Also shown in FIG. 5 are the intensity levels recorded by a single detector for the three positions. In position A, the scattered signals from the red LEDs 1R and 3R are lost because they miss both the red and green lines. The scatter light from the green LEDs, 2G and 4G is attenuated because that light is scattered from the red stripe. In position B, the scattered signals from all LEDs are at their largest because the red LEDs 1R and 3R illuminate the red stripe and the green LEDs, 2G and 4G, illuminate the green stripe. In position C, the scattered signals from the green LEDs, 2G and 4G are lost because they miss the target, and the signals from the red LEDs are attenuated because they are scattering from the red stripe. As this simple example illustrates, the intensity of the scattered light observed by the detector can be used to identify the existence and location of features on the target surface. Further, when the light emitted from the individual LEDs in the array are pulsed so as to substantially eliminate covariance between the red and green diodes, a single detector can be use to detect the scattered light from the target.

Figure 6:
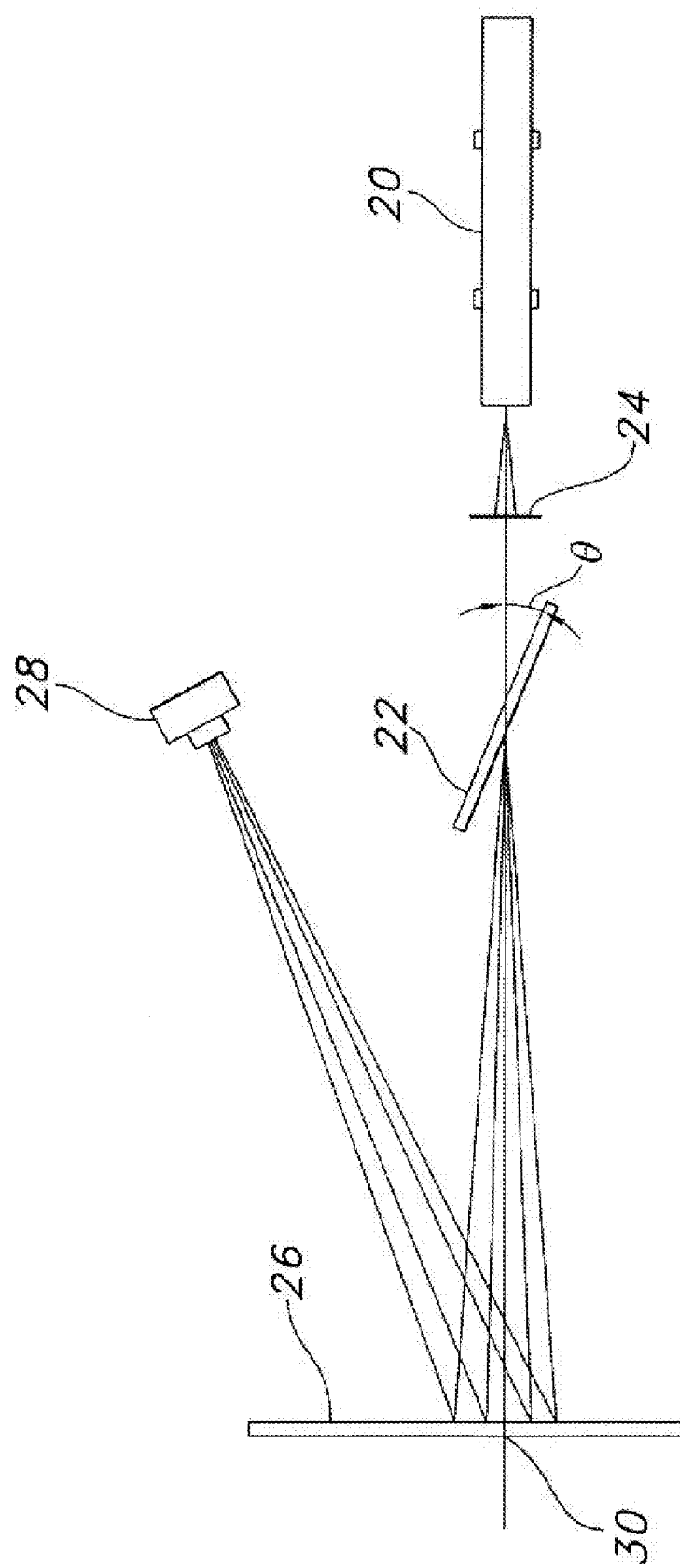
FIG. 6 is a schematic plan view of a simplified form of an equipment setup used to collect scattered light images from a slide surface.

FIG. 6 is a schematic depiction of a simplified form of an equipment setup used to collect scattered light images from a target surface demonstrating some of the principles of the invention. In this simplified setup, a helium-neon (HeNe) laser 20 is used as the light emitting source. The laser 20 directs a collimated modulated light toward a target surface 22, specifically illustrated as a slide. A spatial filter 24 is interposed between the laser 20 and target surface 22 to eliminate stray light output from the laser 20. As the light from the laser 20 strikes an analyte on the target surface, represented by the slide 22, the interaction between the light and the analyte creates light scatter. A white image plane 26 is shown in the path of the scattered light, which image plane reflects the scattered light to a detector 28, specifically shown in the form of a digital camera. An aperture 30 is provided in the image plane 26 to allow the bulk of the unscattered light to pass through to a light dump (not shown), and to limit the dynamic range of the scattering signal to be captured by the detector 28.

Figure 7:
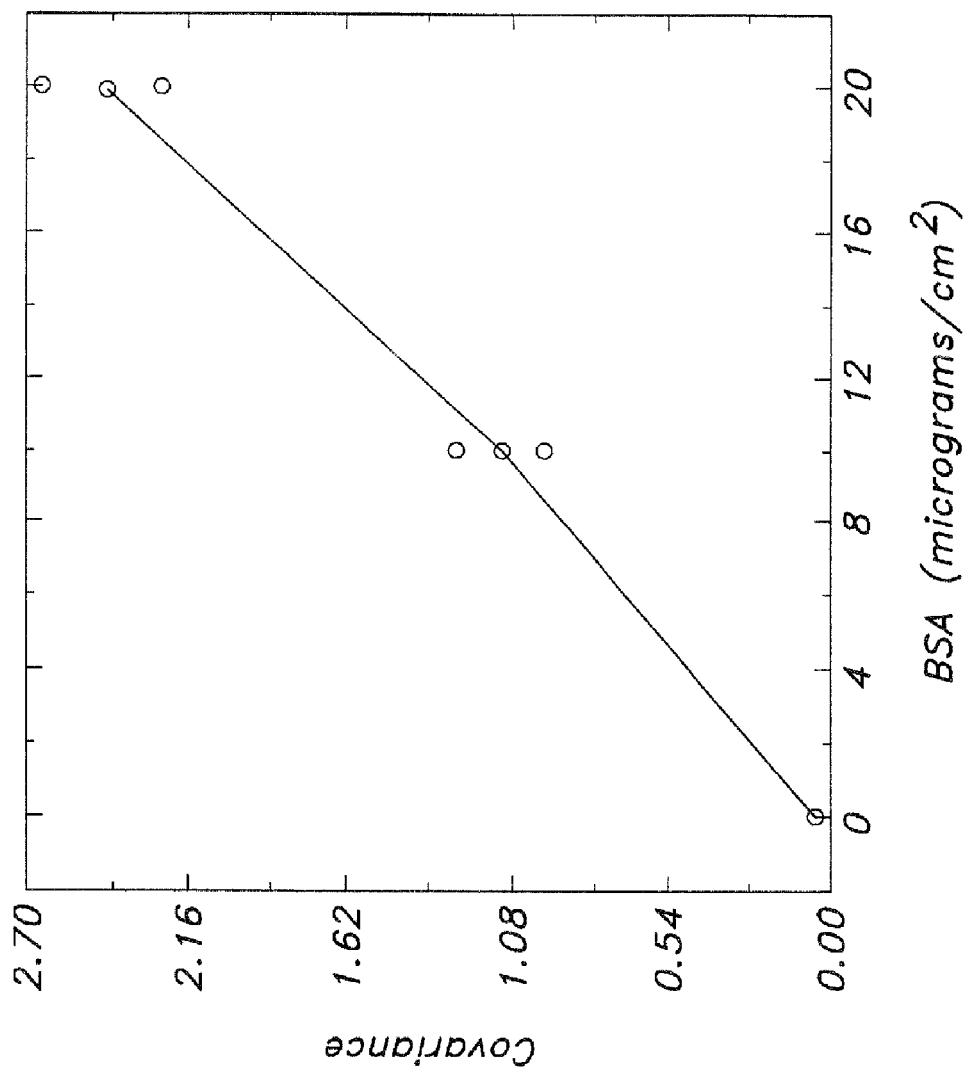
FIG. 7 is a graph depicting an exemplary proportionality between the amount of scattered light received by a photodetector and the amount of analyte on a target surface.

As shown in FIG. 7, the covariance between the collected light and the applied pulse sequence, which is proportional to the amount of scattered light, is in turn proportional to the amount of analyte on the target surface 22. In accordance with the principles of the illustrated exemplary embodiment, this correlation is used to determine the presence or absence of the analyte on the target surface, and, if the analyte is present, to further determine whether the amount of analyte is below acceptable limits.

As may be apparent to those skilled in the art, the present invention differs from approach taken in traditional spectroscopic analysis. In traditional analysis, data are captured by a detector, and thereafter analyzed. In contrast, the present approach uses preexisting empirically derived analytical information about the spectral reflectance characteristics of an analyte or product, and the analyte or characteristic of interest is recognized when the detected values of scattered light correspond to the values of that pre-existing empirically derived information. In this way, a surface or product can be tested quickly to determine the location, identity and quantification of an expected analyte or characteristic. To achieve this result, empirically derived information about the spectral reflectance characteristics of the analyte or product of interest is first identified through traditional spectrographic methods. With that information, discriminating scattering and absorption bands of the analyte or product characteristic of interest, e.g., information about the position and strengths of absorption bands that are unique to the analyte or product of interest and that can be used to identify and distinguish the analyte or characteristic of interest from other materials or conditions, are then identified. Wavelengths of collimated light that will produce scattered light within the discriminating scattering and absorption bands are then selected to be emitted toward the target surface. Once the appropriate wavelengths are determined, the number of diodes, and the position of the diodes can be determined. The number and frequency of wavelengths needed will, of course, depend upon the analyte or characteristic of interest. As noted above, however, the modulations of each of the wavelengths preferably are selected so as to be uncorrelated to any other of the wavelengths in order to permit the single wide band light detector to differentiate between scattered light from different diodes. The light emitting source is then programmed to emit collimated light at the wavelengths chosen to identify and distinguish the analyte or characteristic of interest at modulations that are uncorrelated to each other.

It sometimes is desirable not only to locate and identify an analyte of interest, but also to analyze the concentration of that analyte. By mathematical analysis of the spectral reflectance information for a particular analyte, which can be done, for example, by doing a principal component analysis and least squares regression, the fraction of each wavelength needed to differentiate between different concentrates of the analyte of interest can be determined. With that information, the light emitting source can be coded not only to modulate uncorrelated wavelengths, but also to vary the amount of energy per unit time that is emitted at each wavelength. This variation in the amount of energy emitted can be achieved by either varying the intensity of emission, or by adjusting the duty cycle of the modulated signal. In the pulse sequence illustrated above, for example, the duty cycle of the pulse for selected frequencies could be modified to vary the amount of energy emitted per unit time. Optimally, the number frequencies emitted and amount of energy emitted per unit time are selected to produce a light detector signal that varies linearly proportionally with analyte concentration. Thus, by selecting wavelengths that discriminate the analyte or characteristic of interest from other expected analytes or characteristics, modulating the wavelengths so as to substantially eliminate covariance, and emitting disparate levels of light energy at different wavelengths, the location, identity and concentration of an analyte of interest can be rapidly determined.

In one exemplary embodiment, complementary randomized integrated sensing and processing is used to generate modulation sequences so that by using a single detector, the identity of the signal originating from each diode light source and scattered back from the target surface can be uniquely identified (as in ordinary integrated sensing and processing), but also the total signal integrated over all pulse sequences or modulation frequencies is directly proportional to the analyte concentration. In ordinary integrated sensing and processing using Hadamard or orthogonal pseudorandom codes, or sine waves of different frequencies, the intensity of all of the pulses or frequencies is the same. The coding process encodes spatial and frequency information. By using complementary randomized integrated sensing and processing techniques, and varying the duty cycle of orthogonal pseudorandom codes, the integrated detector signal can be made directly proportional to the concentration of a specific target analyte. To accomplish the technique of this exemplary embodiment, a different table of pulse sequences for each diode is used for each target analyte.

By integrating the detector signal for one pulse sequence length, complementary randomized integrated sensing and processing can be implemented with 0 or 1 pulses. The duty cycle of the sequences can then be used to control the amount of light delivered at each wavelength. When using this scheme, there are as many levels of intensity resolution as there are bits in the orthogonal pseudorandom pulse sequence. When there are many diodes in the emitter head, the pulse sequence is longer and there are more levels of resolution.

In a given position, the sensor could measure the reflectance of a point for a particular wavelength by turning on the single laser diode directed at the point and measuring the photodetector's response. However, the noise level present in the photodetector is significant when only one diode is illuminated. Instead, the coding scheme of this exemplary embodiment uses Walsh-Hadamard pseudo-random sequence of light pulses sampled in each position to increase the signal to noise ratio of samples measured at each point.

Code sequence generation and the inverse transformation are done using Matlab functions. The Hadamard function in Matlab generates Hadamard matrices (square, symmetric matrices) if N, N/12, or N/20 is a power of 2. the sequences generated from these matrices are always of length N−1 (N is always even, so the sequence length is always odd). Hadamard sequences generated using this exemplary scheme have the following properties:

1) All sequences have an equivalent number of 1 and 0 (ON and OFF) states between them. Furthermore, in a particular sequence, the number of 1 states is always one greater than the number of 0 states;

2) The covariance between all sequences is equivalent; and

3) VARIANCE (i)/COVANIANCE (i, j)=−(N−1) for all j not equal to I, where N is the length of the sequence, so covariance between diodes gets lower as the number of diodes and sequence length are increased.

The generation of a binary encoding sequence (1 and 0 coding) using Hadamard matrices (+1 and −1 coding) will be described in the following example of multiplexing 7 signal elements. For this situation, a minimum of 7 sequence resolution elements is necessary, so an 8×8 Hadamard matrix is used. The Hadamard matrices generated by the Matlab function 'Hadamard' have all Is in the first row and column. After generation of the matrix, the first row and column are stripped to give a 7×7 matrix.

```
>> h = hadamard(8)
h =
+1 +1 +1 +1 +1 +1 +1 +1
+1 −1 +1 −1 +1 −1 +1 −1
+1 +1 −1 −1 +1 +1 −1 −1
+1 −1 −1 +1 +1 −1 −1 +1
+1 +1 +1 +1 −1 −1 −1 −1
+1 −1 +1 −1 −1 +1 −1 +1
+1 +1 −1 −1 −1 −1 +1 +1
+1 −1 −1 +1 −1 +1 +1 −1
>> h = h(2: end, 2: end)
h =
−1 +1 −1 +1 −1 +1 −1
+1 −1 −1 +1 +1 −1 −1
−1 −1 +1 +1 −1 −1 +1
+1 +1 +1 −1 −1 −1 −1
−1 +1 −1 −1 +1 −1 +1
+1 −1 −1 −1 −1 +1 +1
−1 −1 +1 −1 +1 +1 −1
```

The matrix elements =1 are then set =0, and the elements =−1 are set =1.

This operation generates the final binary pulse sequences. This matrix is symmetric, so the rows or columns give identical sequences. Examination of the covariance matrix of h demonstrates properties 2 and 3 listed above.

```
>> h(find(h == 1)) = 0
h =
−1 0 −1 0 −1 0 −1
0 −1 −1 0 0 −1 −1
−1 −1 0 0 −1 −1 0
0 0 0 −1 −1 −1 −1
−1 0 −1 −1 0 −1 0
0 −1 −1 −1 −1 0 0
−1 −1 0 −1 0 0 −1
>> h = abs(h) [THESE ARE THE BINARY PULSE SEQUENCES]
h =
1 0 1 0 1 0 1
0 1 1 0 0 1 1
1 1 0 0 1 1 0
0 0 0 1 1 1 1
1 0 1 1 0 1 0
```

-continued

```
0 1 1 1 1 0 0
1 1 0 1 0 0 1
>> cov(h) [COVARIANCE MATRIX —RATIO OF VAR/COV IS −6
FOR ALL]
ans =
 0.2857 −0.0476 −0.0476 −0.0476 −0.0476 −0.0476 −0.0476
−0.0476  0.2857 −0.0476 −0.0476 −0.0476 −0.0476 −0.0476
−0.0476 −0.0476  0.2857 −0.0476 −0.0476 −0.0476 −0.0476
−0.0476 −0.0476 −0.0476  0.2857 −0.0476 −0.0476 −0.0476
−0.0476 −0.0476 −0.0476 −0.0476  0.2857 −0.0476 −0.0476
−0.0476 −0.0476 −0.0476 −0.0476 −0.0476  0.2857 −0.0476
−0.0476 −0.0476 −0.0476 −0.0476 −0.0476 −0.0476  0.2857
```

If a square encoding matrix is used, the inverse transformation is easily generated the following 2-step process applied to the encoding matrix (h):

1) Replace each 0 in h by −1
2) Divide the matrix resulting from step 1 by the constant $(N+1)/2$ The same result is achieved in Matlab by using the matrix inverse function 'inv'

```
>> hinv = inv(h) [INVERSE TRANSFORM]
hinv =
 0.2500 −0.2500  0.2500 −0.2500  0.2500 −0.2500  0.2500
−0.2500  0.2500  0.2500 −0.2500 −0.2500  0.2500  0.2500
 0.2500  0.2500 −0.2500 −0.2500  0.2500  0.2500 −0.2500
−0.2500 −0.2500 −0.2500  0.2500  0.2500  0.2500  0.2500
 0.2500 −0.2500  0.2500  0.2500 −0.2500  0.2500 −0.2500
−0.2500  0.2500  0.2500  0.2500  0.2500 −0.2500 −0.2500
 0.2500  0.2500 −0.2500  0.2500 −0.2500 −0.2500  0.2500
```

An example of a signal encoding/recovery is provided here. 'sigs' represents amplitudes of 7 signals to be measured, and a simulated data collection event is generated by multiplying the 'sigs vector by h, which gives the amplitudes of the measured signal at each sequence element as the result. The original desired signals are recovered from the multiplexed signal by multiplying the encoded signal by the inverse transform.

```
>> sigs = [0.1; 0.3; 0.5; 0.02; 0.75; 0.15; 0]
sigs =
    0.1000
    0.3000
    0.5000
    0.0200
    0.7500
    0.1500
         0
>> encoded_signal = h * sigs
encoded_signal =
    1.3500
    0.9500
    1.3000
    0.9200
    0.7700
    1.5700
    0.4200
>> original_signal = hinv * encoded_signal
original_signal =
    0.1000
    0.3000
    0.5000
    0.0200
    0.7500
    0.1500
    0.0000
```

The above method for generating binary pulse sequences can be used to generate N×N sequences, which is the minimum size necessary for encoding N elements. This is useful if the number of elements you are trying to encode happens to satisfy the constraint that $(N+1)$, $(N+1)/12$, or $(N+1)/20$ is a power of 2. If this is not the case, any family of sequences with a greater number of resolution points than the number of elements you are trying to code can be used. Simply taking the first N rows or columns of an MXM encoding matrix (M>N) gives the desired binary pulse sequences. The properties (i.e., the 3 Hadamard properties described above) of the sequences generated in this way are equivalent to those of the MXM case. For example, if you desire to encode 5 elements using the method described here, the choices of sequence lengths are 3, 7, 12, . . . . For this case, you could choose the first 5 sequences of the 7×7 encoding matrix described above in the first portion of the example.

The speed with which the above-described method and system detects analytes and characteristics of interest is achieved by the use of stored pulse emission tables containing pulse sequences in the memory of the processor 17. By pre-analyzing the analytes or characteristics of interest, the wavelengths and energy levels that will produce a scattered light pattern identifying an analyte or characteristic of interest and distinguishing it from other expected substances or characteristics of the target can be identified. By knowing what wavelengths to emit, and what scattered light characteristics can be expected when the emitted light strikes a particular analyte or characteristic of interest, the light detector signal (e.g., voltage or current) can be used to directly evaluate various concentration levels of the analyte. Alternatively, multiple analytes and spatial characteristics can be determined simultaneously by comparing an ensemble of detector signals to a spectral database also maintained in memory. The system can be designed so that an alarm is triggered whenever there is a correspondency (or lack of correspondency) between the scattered light detected and the spectral reflectance values in the spectral reflectance database stored in memory associated with the processor.

The speed with which the above describes system and method detects analytes or characteristics of interest is dependent upon the existence and use pre-existing tables containing spectral emission values. Thus, in environments where the nature of an analyte of interest in not easily predictable, it may be desirable to use the system in conjunction with another system capable of analyzing a broad range of analytes. This system can be used independently, however, in environments, such as a pharmaceutical environment, where there is a limited number of analytes of interest reasonably can be expected. In such environments, the above described system can be used to rapidly inspect products for predefined defects or problems. For example, the system and method can be used to inspect pharmaceutical tablets for hardness and moisture content. Further, unlike more traditional inspection methods, it is not necessary to limit the inspection to samples. The above described spectroscopic system and method can determine whether a particular tablet has certain predefined characteristics in nanoseconds, and can inspect every tablet manufactured, without damaging or wasting the tablet. This system and method also can be used to inspect sterile or injectable products, such as medications, IV bags and vials, and determine whether those types of products have certain expected characteristics. For example, a vaccine of a particular concentration would have an expected amount of light scattering. Each package of the vaccine could be spectroscopically inspected by the above described techniques, and any package that did not have the expected light scattering could be inspected immediately upon manufacture, and the manufacturing stopped immediately if defective product were detected.

The illustrated system also can be used to determine whether a pharmaceutical or other type of product as a predetermined physical feature or location. It may be desirable, for example, to conduct shape testing for pharmaceutical pills or capsules. For this purpose, a table or other database is stored in memory with empirically derived spatial emission values representative of at least one discriminating spatial characteristic (such as a predetermined shape) or other attribute of an article to be tested. Modulated light having a plurality of different wavelengths of collimated light is then directed toward the article with different wavelengths of the plurality of wavelengths being uncorrelated to each of the other modulated wavelengths. This will substantially eliminate covariance between the light of differing wavelengths. Modulated light also is emitted having a plurality of different aim points with the different modulations being uncorrelated to each of the other modulated aim points so as to eliminate covariance between the light of differing aim points. A single detector can then be used to detect light scattered back from the article. A signal (which can be the presence or absence of a physical parameter) can then be generated when the scattered light received by the detector corresponds to the spatial emission values in the tables. In this way, the system can determine whether the article has a predetermined shape or other physical feature.

The foregoing descriptions of the exemplary embodiments of the invention have been presented for purposes of illustration and description only. They are not intended to be exhaustive or to limit the invention to the precise forms disclosed, and modifications and variations are possible and contemplated in light of the above teachings. While a number of exemplary and alternate embodiments, methods, systems, configurations, and potential applications have been described, it should be understood that many variations and alternatives could be utilized without departing from the scope of the invention. It should be reiterated that not all aspects of the invention need to be used in combination with all other aspects, and a variety of combinations of such aspects are possible.

Thus, it should be understood that the embodiments and examples have been chosen and described in order to best illustrate the principals of the invention and its practical applications to thereby enable one of ordinary skill in the art to best utilize the invention in various embodiments and with various modifications as are suited for particular uses contemplated. Accordingly, it is intended that the scope of the invention be defined by the claims appended hereto.

What is claimed is:

1. A system for determining in situ the presence and concentration of an analyte of interest on a target surface of an object, comprising:
   a light emitting source, the light emitting source being capable of emitting modulated light having a plurality of different wavelengths of collimated light toward a target surface to be tested for an analyte of interest, the different modulations of the plurality of wavelengths being both uncorrelated to the each of the other modulated wavelengths so as to substantially eliminate covariance between light of differing wavelengths, and varying in the amount of light energy per unit time emitted toward the target surface;
   a wide band light detector for detecting light scattered back from the target surface, the light detector receiving light scattered from the target surface without intervening focusing optics; and
   a processor for calculating the covariance of the scattered light received by the light detector and predetermined spectral emission values, using said calculation to generate a signal representative of the presence or absence of the analyte of interest and, if the analyte of interest is present, using the light detected by the light detector over a multiple of wavelengths to generate a signal representative of the analyte concentration.

2. A system as recited in claim 1 wherein the predetermined reflectance emission values are empirically derived.

3. A system as recited in claim 2 wherein the amount of light energy per unit time emitted toward the target surface is varied by varying the intensity of light emitted at different modulations of the plurality of the wavelengths.

4. A system as recited in claim 2 wherein the amount of light energy per unit time emitted toward the target surface is varied by varying the duty cycle of the emitted light.

5. A system as recited in claim 4 wherein the light emitting source modulates each of the pulses of different wavelengths with a different orthogonal pulse sequences uncorrelated to the other modulated wavelengths, and the amount of light per unit time emitted toward the target surface is varied by varying the duty cycle of the pulses.

6. A system as recited in claim 1 further including a memory associated with the processor, the memory having at least one stored table of spectral emission values representative of discriminating spectral reflectance characteristics of an analyte of interest, the signal of the processor being dependent upon the correspondency between the scattered light received by the detector and the spectral emission values in at least one of the stored tables.

7. A system as recited in claim 6 wherein the memory has a plurality of stored tables of spectral emission values, the plurality of stored tables having spectral emission values representative of multiple levels of concentration of an analyte of interest.

8. A method of analyzing a surface for an analyte of interest in situ comprising the steps of:
   creating a database of spectral emission values representative of discriminating spectral reflectance characteristics of an analyte of interest;
   emitting modulated light having a plurality of different wavelengths of collimated light toward a surface with the different modulations of the plurality of wavelengths being uncorrelated to each of the other modulated wavelengths so as to substantially eliminate covariance between light of differing wavelengths;
   using a single wide band detector for detecting light scattered back from the surface in at least the ultraviolet, visible light and infrared ranges of the electromagnetic spectrum; and
   generating a signal when the scattered light detected by the detector corresponds to the spectral emission values in the database.

9. A method as recited in claim 8 wherein the plurality of wavelengths of collimated light emitted toward the surface are selected to correspond to discriminating scattering and absorption bands of an analyte of interest.

10. A method as recited in claim 9 wherein the light detector receives scattered light from the surface without intervening focusing optics.

11. A method as recited in claim 9 wherein the amount of light energy per unit time emitted toward the surface is varied selectively among the different modulations of wavelengths to vary the amount of scattered light from an analyte of interest as a function of the analyte's concentration.

12. A method as recited in claim 11 wherein the selection of frequencies emitted from the light source and the spectral reflectance values in the database are empirically derived.

13. A system for validating cleaning of pharmaceutical process equipment, comprising:
    a light emitting source, the light emitting source being capable of emitting modulated light pulses having a plurality of different wavelengths of collimated light toward a target surface of pharmaceutical process equipment to be tested,
    the light emitting source modulating the pulses of each of the different wavelengths with a different orthogonal pulse sequence relative to the other modulated wavelengths so as to substantially eliminate covariance between pulses of differing wavelength;
    a wide band light detector for detecting light scattered from the target surface in at least the ultraviolet, visible light and infrared ranges of the electromagnetic spectrum, the detector being spaced from the light emitting source;
    a processor; and
    a memory associated with the processor, the memory having a spectral database of spectral emission values representative of discriminating spectral reflectance characteristics of an analyte of interest, the processor being operative to generate a signal in response to correspondence between scattered light received by the detector and the spectral reflectance values the spectral database.

14. A system as recited in claim 13 wherein the light emitting source includes an array of light-emitting laser diodes.

15. A system as recited in claim 14 wherein each of the diodes in the array is arranged in a predetermined spatial relationship to the other diodes, with the position of each diode selected to correspond to a different position of the target surface.

16. A method of determining whether a pharmaceutical product has a predetermined attribute, comprising:
    creating a database of spectral emission values representative of at least one discriminating spectral reflectance characteristic of a predetermined attribute of a pharmaceutical product;
    emitting modulated light having a plurality of different wavelengths of collimated light toward the product with the different
    modulations of the plurality of wavelengths being uncorrelated to each of the other modulated wavelengths so as to substantially eliminate covariance between light of differing wavelengths;
    using a single detector for detecting light scattered back from the product; and
    generating a signal as a function of whether the scattered light received by the detector corresponds to the spectral reflectance values in the spectral database.

17. A method as recited in claim 16 further including the step of selecting the wavelengths of the emitted light to correspond to discriminating spectral reflectance characteristics of the analyte of interest.

18. A method as recited in claim 17 wherein the selection of wavelengths of emitted light is based upon empirical data.

19. A method as recited in claim 17 wherein the amount of light energy emitted per unit time is varied at selected of the emitted wavelengths to increase the amount of scattered light as a function of the concentration of the analyte of interest.

20. A method as recited in claim 17 wherein the selection of wavelengths of collimated light emitted toward the product is based upon empirically derived data.

21. A method as recited in claim 17 wherein the detector receives light scattered from the product without intervening focusing optics.

22. A method for determining whether a product has a predetermined physical feature or location, comprising:
    creating a database of spatial emission values representative of at least one discriminating spatial emission characteristics of a predetermined attribute of a product to be tested;
    emitting modulated light having a plurality of different wavelengths of collimated light toward a plurality of aim points on the product to be tested with the different modulations of the plurality of wavelengths directed to each aim point being uncorrelated to each of the other modulated wavelengths and each of the aim points being uncorrelated to each of the other aim points so as to substantially eliminate covariance between light of differing wavelengths and to substantially eliminate covariance of light between differing aim points;
    using a single wide band detector for detecting light scattered back from the plurality of aim points in at least the ultraviolet, visible light and infrared ranges of the electromagnetic spectrum; and
    generating a signal when the scattered light detected by the detector corresponds to the spatial emission values in the database.

23. A system for determining in situ the presence and concentration of an analyte of interest on a target surface of an object, comprising:
    a collimated light emitting array having a plurality of light emitting elements with each of the light emitting elements being capable of emitting a light pulse corresponding to a pulse sequence applied to the element, the light emitting array being capable of emitting modulated light having a plurality of different wavelengths of collimated light toward a plurality of different locations on a target surface to be tested for an analyte of interest, the different modulations of the plurality of wavelengths being both uncorrelated to the each of the other modulated wavelengths so as to substantially eliminate covariance between light of differing wavelengths, and varying in the amount of light energy per unit time emitted toward the target surface;
    a wide band light detector for detecting light scattered back from the target surface, the light detector receiving light scattered from the target surface without intervening focusing optics; and
    a processor for calculating the covariance between scattered light received by the light detector over multiple wavelengths and the pulse sequence applied to each collimated light emitting array element; and
    a memory associated with the processor, the memory having a database of empirically derived spectral emission values representative of spectral emission characteristics of at least one predetermined concentration of the analyte of interest, the processor being operative to generate a signal representative of the concentration of the analyte of interest in response to a correspondence between the covariance of light detected by the detector over multiple wavelengths and the pulse sequence applied to each collimated light emitting array element.

* * * * *